(12) United States Patent
Funaoka

(10) Patent No.: US 11,014,277 B2
(45) Date of Patent: May 25, 2021

(54) RESIN MOLDED ARTICLE AND METHOD FOR PRODUCING RESIN MOLDED ARTICLE

(71) Applicant: TOYOBO CO., LTD., Osaka (JP)

(72) Inventor: Daiki Funaoka, Tokyo (JP)

(73) Assignee: TOYOBO CO., LTD., Osaka (JP)

( * ) Notice: Subject to any disclaimer, the term of this patent is extended or adjusted under 35 U.S.C. 154(b) by 119 days.

(21) Appl. No.: 16/468,543

(22) PCT Filed: Dec. 25, 2017

(86) PCT No.: PCT/JP2017/046360
§ 371 (c)(1),
(2) Date: Jun. 11, 2019

(87) PCT Pub. No.: WO2018/123934
PCT Pub. Date: Jul. 5, 2018

(65) Prior Publication Data
US 2020/0086538 A1 Mar. 19, 2020

(30) Foreign Application Priority Data

Dec. 28, 2016 (JP) .............................. JP2016-256476

(51) Int. Cl.
*B29C 45/14* (2006.01)
*A61M 25/00* (2006.01)
(Continued)

(52) U.S. Cl.
CPC .. *B29C 45/14008* (2013.01); *B29C 45/14819* (2013.01); *B29C 45/37* (2013.01);
(Continued)

(58) Field of Classification Search
CPC .... B29C 45/14819; B29C 2045/14852; B29C 2045/1486; B29C 45/37; B29C 70/84;
(Continued)

(56) References Cited

U.S. PATENT DOCUMENTS

2004/0075198 A1* 4/2004 Schweikert ....... A61M 25/0009
264/464
2005/0040557 A1* 2/2005 Flynn ................ A61M 25/0026
264/248

(Continued)

FOREIGN PATENT DOCUMENTS

CN 105829056 8/2016
JP 56-49208 5/1981
(Continued)

OTHER PUBLICATIONS

Partial machine translation of JP 2006-035630 A dated Feb. 2006 obtained from the espace website. (Year: 2006).*

(Continued)

*Primary Examiner* — Robert B Davis
(74) *Attorney, Agent, or Firm* — Wenderoth, Lind & Ponack, L.L.P.

(57) ABSTRACT

An object of the present invention is to provide a technique by which, when producing a resin molded article using an insert member having low pressure resistance, molding can be easily performed, and deformation of the insert member can be suppressed. A method for producing a resin molded article of the present invention, the method includes the steps of disposing an insert member in a cavity of a mold; performing injection of molten resin into the cavity; terminating the injection on and after the molten resin reaches an overflow portion in the cavity and before the molten resin fills the overflow portion; and separating resin in the overflow portion.

12 Claims, 4 Drawing Sheets

(51) Int. Cl.
  *B29C 45/37* (2006.01)
  *B29L 23/00* (2006.01)
  *A61M 25/10* (2013.01)

(52) U.S. Cl.
  CPC ..... *A61M 25/0026* (2013.01); *A61M 25/1036* (2013.01); *A61M 2025/0037* (2013.01); *B29C 2045/1486* (2013.01); *B29C 2045/14852* (2013.01); *B29C 2945/76013* (2013.01); *B29C 2945/76254* (2013.01); *B29L 2023/00* (2013.01)

(58) Field of Classification Search
  CPC .. B29C 70/845; B29C 70/88; A61M 25/0026; A61M 2025/0037; A61M 2025/0039; A61M 25/1036
  See application file for complete search history.

(56) References Cited

U.S. PATENT DOCUMENTS

| | | | |
|---|---|---|---|
| 2014/0187961 A1* | 7/2014 | Yamakoshi | A61B 1/00089 600/467 |
| 2015/0174803 A1 | 6/2015 | Newman et al. | |
| 2015/0336311 A1 | 11/2015 | Newman et al. | |
| 2016/0278219 A1 | 9/2016 | Ito | |
| 2017/0080181 A1 | 3/2017 | Shiono et al. | |
| 2017/0136207 A1 | 5/2017 | Shiono et al. | |

FOREIGN PATENT DOCUMENTS

| | | |
|---|---|---|
| JP | 2006-35630 | 2/2006 |
| JP | 2015-126612 | 7/2015 |
| JP | 2016-10484 | 1/2016 |
| JP | 2016-10485 | 1/2016 |

OTHER PUBLICATIONS

International Search Report dated Feb. 27, 2018 in International (PCT) Application No. PCT/JP2017/046360.
Office Action dated Nov. 6, 2020 in corresponding Chinese Patent Application No. 201780080854.7, with English translation.
Office Action dated Feb. 9, 2021 in corresponding Taiwanese Patent Application No. 106146117, with English-language translation.

* cited by examiner

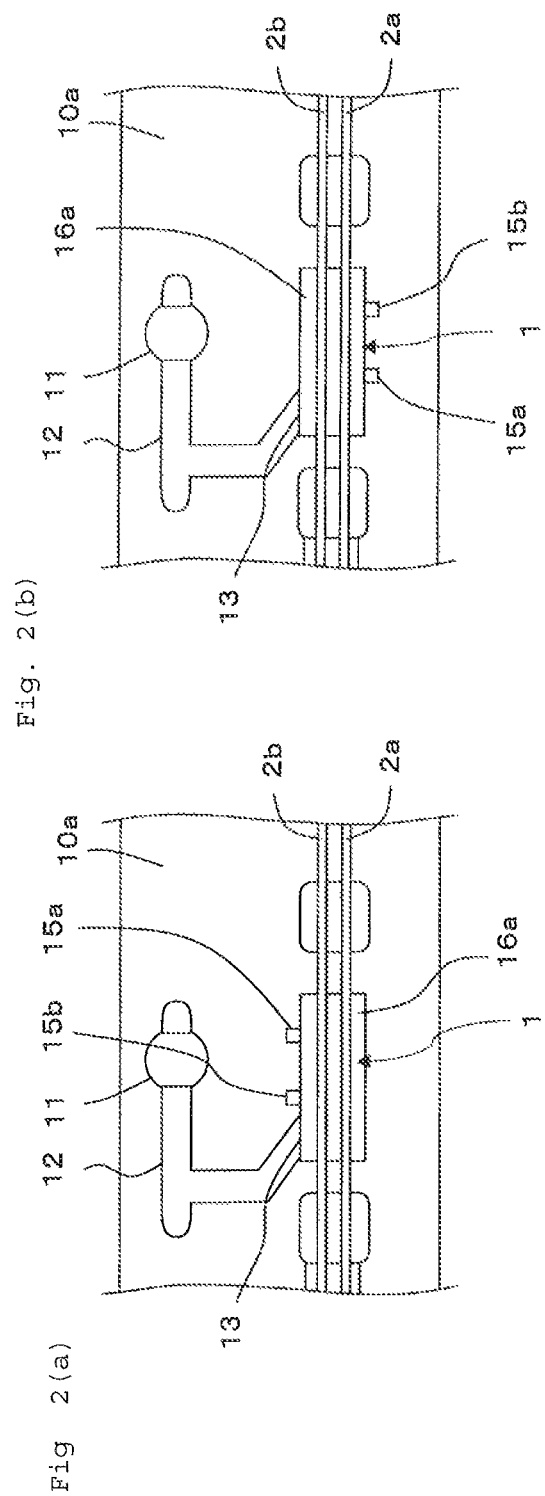

RESIN MOLDED ARTICLE AND METHOD FOR PRODUCING RESIN MOLDED ARTICLE

TECHNICAL FIELD

The present invention relates to a resin molded article and a method for producing a resin molded article,

BACKGROUND ART

Catheters are conventionally used to give medicines, nutrition, etc. to patients and perform various treatments on patients. Some catheters have a plurality of tubes of which the branched parts are sealed with resin such as an adhesive.

For example, Patent Document 1 discloses a technique by which, when producing a balloon catheter, an inner tube and an outer tube into which core bars are inserted are disposed in a mold, and molten resin is injected to form a branched part of a line.

A molding method in which an insert member is thus disposed in a mold, and the mold is filled with resin, thereby integrating the insert member and the filled resin is called insert molding. Such insert molding is also performed in the field of electronic components.

For example, Patent Document 2 discloses a technique by which a circuit board on which electronic components are mounted is set in a mold, and an outer case is formed by molding.

RELATED ART DOCUMENTS

Patent Documents

Patent Document 1: JP-A-2016-10484
Patent Document 2: JP-A-2015-126612

SUMMARY OF THE INVENTION

Problems to be Solved by the Invention

As described in Patent Document 1, when injection molding is performed on a flexible tube used for a catheter or the like, the tube may be crushed by injection pressure. Therefore, it is necessary to insert a core bar into the tube before resin molding, and hence there is a problem in that resin molding cannot be easily performed.

As described in Patent Document 2, when resin molding is performed on a circuit board on which electronic components are mounted, since the electronic components such as an electric field capacitor and an oscillator cannot withstand pressure during injection molding, the mounting portion must be exposed to a non-cavity space that is not filled with resin, and hence there is a problem in that resin molding cannot be easily performed.

The present invention has been made in view of the above-mentioned circumstances, and an object of the present invention is to provide a technique by which, when producing a resin molded article using an insert member having low pressure resistance, molding can be easily performed, and deformation of the insert member can be suppressed.

Solutions to the Problems

A method for producing a resin molded article of the present invention comprises the steps of disposing an insert member in a cavity of a mold, performing injection of molten resin into the cavity, terminating the injection on and after the molten resin reaches an overflow portion in the cavity and before the molten resin fills the overflow portion, and separating resin in the overflow portion. By this configuration, when producing a resin molded article using an insert member having low pressure resistance, molding can be easily performed, and deformation of the insert member can be suppressed.

The configuration of the present invention is as follows.

(1) A method for producing a resin molded article, the method comprising the steps of:
disposing an insert member in a cavity of a mold;
performing injection of molten resin into the cavity;
terminating the injection on and after the molten resin reaches an overflow portion in the cavity and before the molten resin, fills the overflow portion; and
separating resin in the overflow portion.

(2) The method for producing a resin molded article according to (1), wherein the insert member is one or more tubes.

(3) The method for producing a resin molded article according to (2), wherein, under compression load of 100 gf per 1 cm of a length of the tubes by a pressure element, the tubes have a height in a direction of compression of $7/10$ or less of a height in the direction of compression prior to applying the compression load.

(4) The method for producing a resin molded article according to (1), wherein the insert member is an electronic component having a hollow portion.

(5) The method for producing a resin molded article according to any of (1) to (4), wherein a molding temperature is 100° C. or higher and 250° C. or lower.

(6) The method for producing a resin molded article according to any of (1) to (5), wherein a pressure of the injection is 0.1 MPa or more and 50 MPa or less.

(7) The method for producing a resin molded article according to any of (1) to (6), wherein a pressure applied onto the insert member after the injection is 5 MPa or less.

(8) The method for producing a resin molded article according to any of (1) to (7), wherein a melt viscosity at 200° C. of the resin is 5 dPa·s or more and 5000 dPa·s or less.

(9) The method for producing a resin molded article according to any of (1) to (8), wherein the resin is at least one hot-melt resin selected from a group consisting of a polyester-based hot-melt resin, polystyrene-based hot-melt resin, polyolefin-based hot-melt resin, polyurethane-based hot-melt resin, polyamide-based hot-melt resin, and reactive hot-melt resin.

(10) The method for producing a resin molded article according to any of (1) to (8), wherein the resin is at least one thermosetting resin selected from a group consisting of a phenolic resin, unsaturated polyester resin, diallyl phthalate resin, and polyimide resin.

(11) The method for producing a resin molded article according to any of (2), (3), and (5) to (10), wherein no core bar is inserted into the tubes.

(12) A resin molded article comprising one or more tubes and a sealed part in which at least part of the tubes is sealed with resin, wherein, under compression load of 100 gf per 1 cm of a length of the tubes by a pressure element, the tubes have a height in a direction of compression of $7/10$ or less of a height in the direction of compression prior to applying the compression load.

(13) The resin molded article according to (12), wherein a ratio of a minor diameter to a major diameter of the tubes in the sealed part is 0.9 or more.

(14) The resin molded article according to (12) or (13), wherein a ratio of a minor diameter to a major diameter of the tubes in the sealed part at a position 1 cm away from one end of the sealed part in an axial direction of the tubes is the same as or smaller than a ratio of a minor diameter to a major diameter of the tubes in an exposed part that is not sealed with the resin at a position 1 cm away from the one end.

(15) The resin molded article according to any of (12) to (14), wherein the tubes in the sealed part have a minimum thickness of 0.05 mm or more and 0.5 mm or less.

(16) The resin molded article according to any of (12) to (15), wherein the tubes have a branched part, and the branched part is sealed with the resin.

(17) The resin molded article according to any of (12) to (16), wherein the resin molded article is an injection molded article.

Effects of the Invention

According to the present invention, by the above-described configuration, when producing a resin molded article using an insert member having low pressure resistance, molding can be easily performed, and deformation of the insert member can be suppressed.

BRIEF DESCRIPTION OF THE DRAWINGS

FIGS. 2(a) and 2(b) are plan views of a lower mold in which an insert member is disposed.

MODE FOR CARRYING OUT THE INVENTION

The inventor of the present invention conducted intensive studies to provide a technique by which, when producing a resin molded article using an insert member having low pressure resistance, molding can be easily performed, and deformation of the insert member can be suppressed. As a result, the inventor has found that an intended object can be achieved by a method for producing a resin molded article, the method comprising the steps of disposing an insert member in a cavity of a mold, performing injection of molten resin into the cavity, terminating the injection on and after the molten resin reaches an overflow portion in the cavity and before the molten resin fills the overflow portion, and separating resin in the overflow portion. Thus, the present invention has been made based on this finding.

Hereinafter, the method for producing a resin molded article according to the present invention will be described with reference to the drawings. The production method of the present invention is characterized by the above-mentioned steps, and steps other than the above-mentioned steps are not particularly limited as long as they are usually used.

Figure 1A:
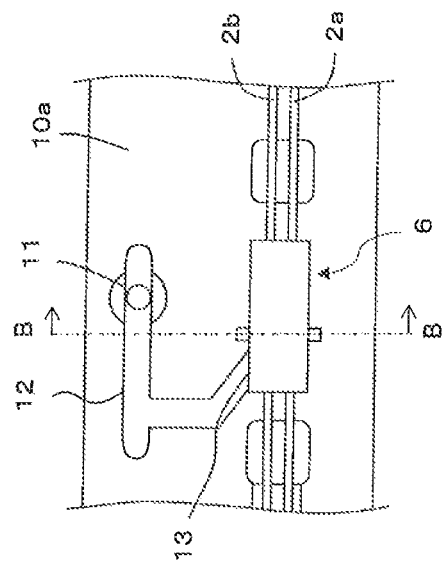
FIG. 1(a) is a plan view of a lower mold in which an insert member is disposed.
Figure 1B:
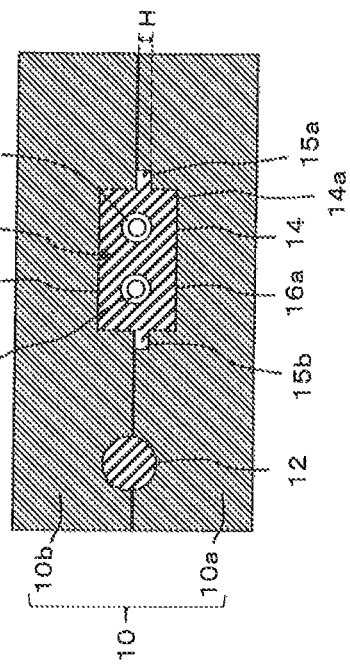
FIG. 1(b) is a cross-sectional view of a mold in which an insert member is disposed.
Figure 1C:
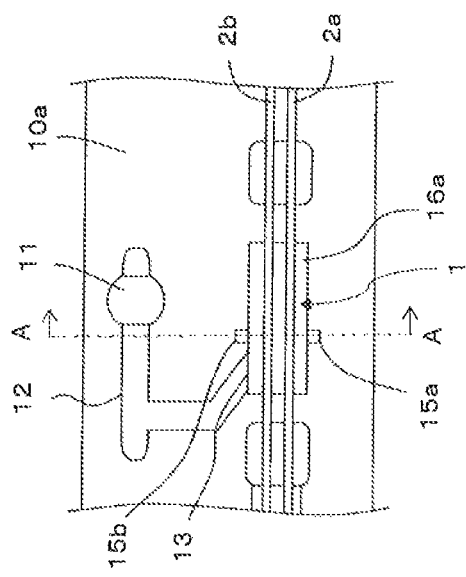
FIG. 1(c) is a plan view of a lower mold after injection of molten resin.
Figure 1D:
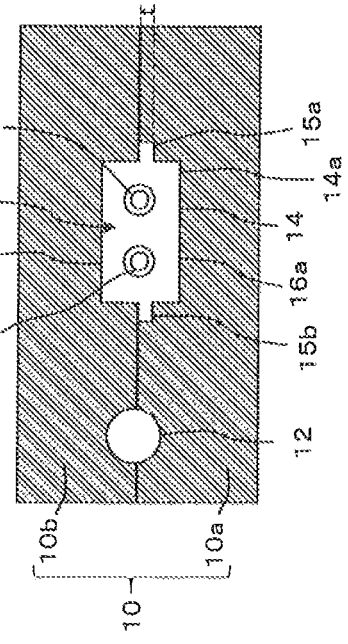
FIG. 1(d) is a cross-sectional view of a lower mold after injection of molten resin.

FIG. 1(a) is a plan view of a lower mold in which an insert member is disposed. FIG. 1(b) is a cross-sectional view of a mold in which an insert member is disposed, as taken along the line A-A in FIG. 1(a). FIG. 1(c) is a plan view of a lower mold after injection of molten resin. FIG. 1(d) is a cross-sectional view of a lower mold after injection of molten resin, as taken along the line B-B in FIG. 1(c).

Figures 3A, 3B:
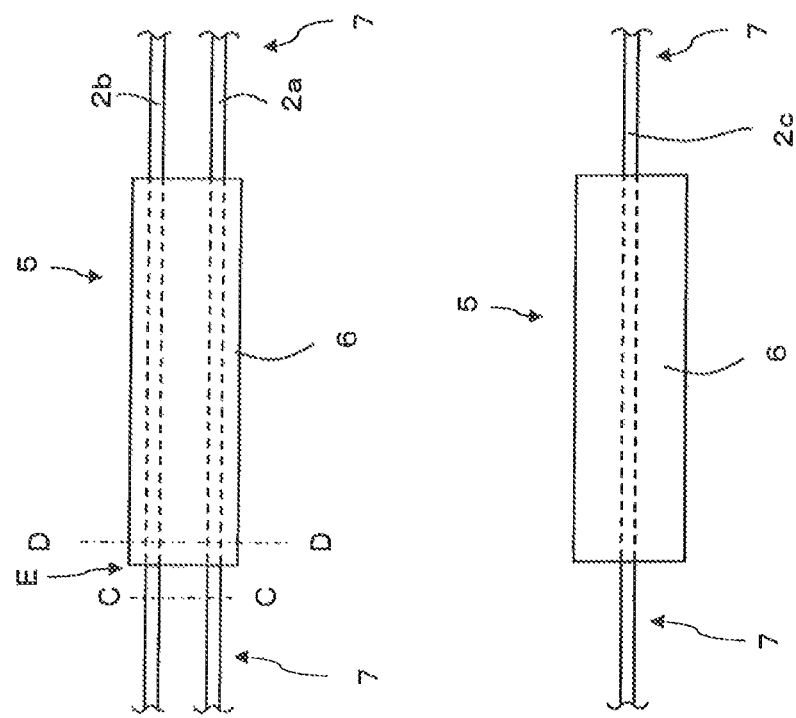
FIGS. 3(a) and 3(b) are plan views of a resin molded article of the invention.

In the method for producing a resin molded article of the present invention, a mold 10 as shown in FIG. 1 can be used. First, as shown in FIG. 1(a), an insert member 1 is disposed in a recess 16a of a lower mold 10a, Next, as shown in FIG. 1(b), the inner surface of the lower mold 10a is brought into contact with and fixed to the inner surface of an upper mold 10b, so that the insert member 1 is located in a cavity 14 formed by the recess 16a of the lower mold 10a and a recess 16b of the upper mold 10b. Then, molten resin is injected into the cavity 14 through a sprue 11, a runner 12 and a gate 13. The injection of the molten resin is terminated after the molten resin reaches overflow portions 15a and 15b in the cavity 14 and before the molten resin fills the overflow portions 15a and 15b. Then, the resin in the overflow portions 15a and 15b is separated to obtain a resin molded article 5 as shown in FIG. 3(a).

The method for producing a resin molded article of the present invention has the most important feature in that the injection of the molten resin is terminated on and after the molten resin reaches the overflow portions 15a and 15b and before the molten resin fills the overflow portions 15a and 15b. Such easy control can reduce pressure applied to the insert member 1 via leaks of resin to the overflow portions and can thereby suppress deformation of the insert member 1.

The overflow portions 15a and 15b are preferably located at the flow terminal of the molten resin in the mold 10. This makes it possible to easily suppress deformation of the insert member 1.

As shown in FIGS. 1(b) and 1(d), the thickness H of inlet parts of the overflow portions 15a and 15b in contact with a cavity 14a in a main body is preferably smaller than the thickness of the insert member 1. This allows to the molten resin to be easily injected into the cavity 14a in the main body in which the insert member 1 is disposed. The thickness H is more preferably ½ or less, further preferably ⅓ or less, still further preferably ¼ or less of the thickness of the insert member 1. When the thickness H is 1/20 or more of the thickness of the insert member 1, deformation of the insert member 1 can be easily suppressed. The thickness H is preferably 1/20 or more, more preferably 1/10 or more, further preferably ⅙ or more of the thickness of the insert member 1.

The thickness H is preferably the smallest thickness of the cavity in the mold 10. This allows the resin in the overflow portions 15a and 15b to be easy to separate, and in addition, the overflow portions 15a and 15b to be easy to locate at the flow terminal of the molten resin.

The shape of the overflow portions 15a and 15b is not particularly limited, and examples thereof include a polygonal pillar shape, a cylindrical shape, a polygonal truncated pyramid shape, a spherical shape, and a combined shape thereof. In the case of the combined shape, the overflow portions 15a and 15b may have, for example, a shape broadening from the inlet part toward the opposite side to the cavity 14a in the main body.

In FIG. 1(a), when viewed from the insert member 1, the overflow portion 15b is provided on the gate 13 side, and the overflow portion 15a is provided on the side opposite to the gate 13. However, the positions of the overflow portions 15a and 15b are not limited thereto. For example, as shown to FIG. 2(a), the overflow portions 15a and 15b may be provided on the gate 13 side as viewed from the insert member 1, and as shown in FIG. 2(b), the overflow portions

15a and 15b may be provided on the side opposite to the gate 13 as viewed from the insert member 1.

The overflow portions may be provided at not only two positions but also one position or three or more positions. That is, one or more overflow portions may be provided.

Each step will be described in detail below.

For the injection of molten resin, an injection molding machine, a hot melt molding machine or the like can be used. Examples of the injection molding machine include an injection molding machine THX5S1VN manufactured by Nissei Plastic Industrial Co., Ltd. Examples of the hot-melt molding machine include a hot-melt molding machine JWS extruder manufactured by Nordson Corporation, a small electric injection molding machine LS-300 manufactured by Canon Electronics Inc., a hot-melt applicator MX-3106 manufactured by Nordson Corporation, and the like.

A molding temperature (nozzle temperature) varies depending on the type of resin or the like and is not particularly limited. However, when a hot-melt resin is used, the molding temperature is preferably 100° C. or higher and 250° C. or lower. By setting the molding temperature to be 100° C. or higher, the temperature of the resin is likely to become higher than the melting temperature (a melting point if the resin is crystalline, and a glass transition temperature if the resin is non-crystalline), so that the flowability of the resin is improved, and the molten resin can be easily injected into the mold 10. The molding temperature is more preferably 120° C. or higher, further preferably 140° C. or higher, still further preferably 160° C. or higher. By setting the molding temperature to be 250° C. or lower, thermal deterioration of the insert member can be easily suppressed, and decomposition or discoloration of the resin component can be easily suppressed. The molding temperature is more preferably 220° C. or lower, further preferably 210° C. or lower, still further preferably 200° C. or lower.

When the molten resin is a thermosetting resin, the molding temperature (nozzle temperature) is preferably 40° C. or higher and 120° C. or lower. By setting the molding temperature to be 40° C. or higher, the flowability of the resin is improved, and the molten resin can be easily injected into the mold 10. The molding temperature is more preferably 50° C. or higher, further preferably 55° C. or higher, still further preferably 60° C. or higher. By setting the molding temperature to be 120° C. or lower, the resin is hardly cured, so that the molten resin can be easily injected into the mold 10. The molding temperature is more preferably 100° C. or lower, further preferably 90° C. or lower, still further preferably 80° C. or lower.

A mold temperature also varies depending on the type of resin or the like and is not particularly limited. However, when a hot-melt resin is used, the mold temperature is preferably 20° C. or higher and 120° C. or lower. By setting the mold temperature to be 20° C. or higher, the molten resin can be easily injected into the mold 10. The mold temperature is more preferably 30° C. or higher, further preferably 40° C. or higher. By setting the mold temperature to be 120° C. or lower, dips or the like generated on the surface of the resin molded article 5 can be easily reduced. The mold temperature is more preferably 100° C. or lower, further preferably 80° C. or lower.

When a thermosetting resin is used, the mold temperature is preferably 80° C. or higher and 250° C. or lower. By setting the mold temperature to be 80° C. or higher, it becomes easy to cure the molten resin in the mold 10. The mold temperature is more preferably 100° C. or higher, further preferably 120° C. or higher. By setting the mold temperature to be 250° C. or lower, thermal deterioration of the insert member can be easily suppressed, and decomposition or discoloration of the resin component can be easily suppressed. The mold temperature is more preferably 200° C. or lower, further preferably 180° C. or lower.

The injection pressure of the molten resin is preferably 0.1 MPa or more and 50 MPa or less. By setting the injection pressure to be 50 MPa or less, deformation of the insert member 1 can be suppressed, and occurrence of burrs due to a leak of resin through a parting can be easily suppressed. The injection pressure is more preferably 40 MPa or less, further preferably 30 MPa or less, still further preferably 20 MPa or less. By setting the injection pressure to be 0.1 MPa or more, dips and wrinkles generated on the surface of the resin molded article 5 can be easily reduced. The injection pressure is more preferably 0.5 MPa or more, further preferably 2 MPa or more, still further preferably 5 MPa or more.

The injection rate of the molten resin is preferably 1 mm/sec or more and 50 mm/sec or less. By setting the injection rate to be 50 mm/sec or less, deformation of the insert member 1 can be suppressed, and occurrence of burrs can be easily suppressed. The injection rate is more preferably 40 mm/sec or less, further preferably 30 mm/sec or less, still further preferably 20 mm/sec or less. By setting the injection rate to be 1 mm/sec or more, dips and wrinkles generated on the surface of the resin molded article 5 can be easily reduced. The injection rate is more preferably 5 mm/sec or more, further preferably 10 mm/sec or more.

The injection time of the molten resin is preferably 1 second or more and 10 seconds or less. By setting the injection time to be 1 second or more, deformation of the insert member 1 can be suppressed, and occurrence of burrs can be easily suppressed. The injection time is more preferably 2 seconds or more, further preferably 4 seconds or more. By setting the injection time to be 10 seconds or less, dips and wrinkles generated on the surface of the resin molded article 5 can be easily reduced. The injection time is more preferably 8 seconds or less, further preferably 6 seconds or less.

The pressure applied onto the insert member 1 after terminating the injection of the molten resin is preferably 5 MPa or less. By setting the pressure to be 5 MPa or less, deformation of the insert member 1 can be easily suppressed. The pressure is more preferably 2 MPa or less, further preferably 1.5 MPa or less, still more preferably 1.0 MPa or less, still further preferably 0.5 MPa or less, and most preferably 0 MPa.

The pressure keeping time after injection of the molten resin varies depending on the type of a mold, resin or the like, and is not particularly limited. The pressure keeping time is preferably from 1 to 20 seconds, more preferably from 4 to 15 seconds, further preferably from 6 to 10 seconds.

The cooling time or heating time of the molten resin in the mold 10 varies depending on the type of resin or the like and is not particularly limited. The cooling time or heating time is preferably from 1 to 120 seconds, more preferably from 5 to 80 seconds, further preferably from 10 to 50 seconds.

A method of separation of the resin in the overflow portions 15a and 15b is not particularly limited. The resin in the overflow portions 15a and 15b may be naturally dropped to separate it when taking out the resin molded article 5 from the mold 10, or may be cut using a push cutter, a rotary cutter or an air nipper after taking out the resin molded article 5 from the mold 10. It is preferred that the resin be naturally dropped when taking out the resin in the overflow portions 15a and 15b because the workability is improved.

The melt viscosity at 200° C. of resin to be injected is preferably 5 dPa·s or more and 5000 dPa·s or less. If the melt viscosity is too high, the insert member 1 may be deformed even though the injection rate of the molten resin is low. However, if the melt viscosity is 5000 dPa·s or less, deformation of the insert member 1 can be easily suppressed. The melt viscosity is more preferably 2000 dPa·s or less, further preferably 1000 dPa·s or less, still further preferably 500 dPa·s or less. If the melt viscosity is 5 dPa·s or more, so-called "sniveling" associated with leaks of resin from a nozzle or the like can be easily suppressed. The melt viscosity is more preferably 20 dPa·s or more, further preferably 50 dPa·s or more, still further preferably 100 dPa·s or more.

The melt viscosity at 200° C. of resin to be injected can be determined by the following method. For example, using a flow tester (model: CFT-500C) manufactured by Shimadzu Corporation, a resin sample dried to a water content of 0.1% or less is filled into a cylinder in the center of a heating body set at 200° C., and after the lapse of 1 minute of filling, a load (10 kgf) is added to the sample via a plunger, the melted sample is extruded from a die (hole diameter: 1.0 mm, thickness: 10 mm) at the bottom of the cylinder, and the distance and time of a descent of the plunger may be recorded to calculate a melt viscosity.

When using a tube as an insert member, it is preferable not to insert a core bar into the tube. Insertion of a core bar into a bore of the tube may damage the bore of the tube, and such a damage to the bore of the tube can be avoided by not inserting the core bar. The core bar is a metal rod that does not melt or deform at the above-mentioned molding temperatures. The core bar is made of, for example, stainless steel, iron and the like.

The resin to be injected is preferably, for example, a hot-melt resin or a thermosetting resin. Between these, a hot-melt resin is more preferable.

A hot-melt resin melts when the resin temperature rises, and solidifies when the resin temperature falls, which is a so-called thermoplastic resin. The hot-melt resin includes at least one selected from the group consisting of a polyester-based hot-melt resin, polystyrene-based hot-melt resin, polyolefin-based hot-melt resin, polyurethane-based hot-melt resin, poly amide-based hot-melt resin, and reactive hot-melt resin. Among these, at least one selected from the group consisting of a polyester-based hot-melt resin, polystyrene-based hot-melt resin, polyolefin-based hot-melt resin, polyurethane-based hot-melt resin, and polyamide-based hot-melt resin is preferable, and a polyester-based hot-melt resin is more preferable.

The polyester-based hot-melt resin is formed by reacting a carboxylic acid component with a hydroxyl group component. The carboxylic acid component includes at least one selected from the group consisting of terephthalic acid, isophthalic acid, adipic acid, azelaic acid, sebacic acid, 1,4-cyclohexanedicarboxylic acid, 1,3-cyclohexanedicarboxylic acid, 1,2-cyclohexanedicarboxylic acid, 4-methyl-1,2-cyclohexanedicarboxylic acid, dimer acid, hydrogenated dimer acid, and naphthalenedicarboxylic acid. The hydroxyl group component includes at least one selected from the group consisting of ethylene glycol, 1,2-propanediol, 1,3-propanediol, 1,2-butanediol, 1,3-butanediol, 1,4-butanediol, 2-methyl-1,3-propanediol, 1,5-pentanediol, 1,6-hexanediol, 3-methyl-1,5-pentanediol, dipropylene glycol, diethylene glycol, neopentyl glycol, 2,2,4-trimethyl-1,3-pentanediol, tricyclodecanedimethanol, neopentyl glycol hydroxypivalate, 1,9-nonanediol, 2-methyloctanediol, 1,10-dodecanediol, 2-butyl-2-ethyl-1,3-propanediol, polytetramethylene glycol, polyoxymethylene glycol, and cyclohexanedimethanol. As commercially available products of the polyester-based hot-melt resin, VYLOSHOT (registered trademark) GM-955 manufactured by Toyobo Co., Ltd., or the like can be given.

The polystyrene-based hot-melt resin, includes at least one selected from the group consisting of polystyrene; rubber-modified polystyrene; a styrene-acrylonitrile copolymer; a styrene-rubber polymer copolymer; a styrene-rubber polymer-acrylonitrile copolymer; a styrene-maleimide copolymer, which is a copolymer of styrene and a maleimide monomer such as maleimide and N-phenyl maleimide; and a styrene-acrylamide copolymer, which is a copolymer of styrene and an acrylamide monomer such as acrylamide. Part of the raw material styrene may be replaced with α-methylstyrene, p-methylstyrene, p-t-butylstyrene, o-ethylstyrene, o-p-dichlorostyrene or the like.

The polyolefin based hot-melt resin is a homopolymer or copolymer of olefins such as ethylene, propylene and butane; a copolymer of such olefins with a monomer component that can be copolymerized with the olefins; and their maleic anhydride modified products. The polyolefin-based resin includes at least one selected from the group consisting of polyethylene, polypropylene, an ethylene-vinyl acetate copolymer, an ethylene-ethyl acrylate copolymer, an ethylene-acrylic acid copolymer, an ethylene-methyl methacrylate copolymer, an ethylene-α-olefin copolymer, an ethylene-propylene copolymer, an ethylene-butene copolymer, and a propylene-butene copolymer.

The polyurethane-based hot-melt resin is formed by reacting a hydroxyl group component (prepolymer) with an isocyanate compound (hardening agent). The hydroxyl group component includes at least one selected from the group consisting of polyester polyol, polycaprolactone polyol, polyether polyol, polyalkylene polyol, and polycarbonate polyol. The isocyanate compound includes at least one diisocyanate selected from the group consisting of trimethylene diisocyanate (TDI), hexamethylene diisocyanate (HDI), diphenylmethane diisocyanate (MDI), isophorone diisocyanate (IPDI), and xylylene diisocyanate (XDI).

The polyamide-based hot-melt resin is a polymer having an amide bond in its molecule. The polyamide-based resin includes at least one selected from the group consisting of nylon 6,6, nylon 6,9, nylon 6,10, nylon 6,12, nylon 6, nylon 12, nylon 11, and nylon 4,6.

As the reactive hot-melt resin, moisture-curable urethane hot-melt resin, UV-curable hot-melt resin, and the like can be mentioned.

The thermosetting resin is not particularly limited as long as it is used for injection molding or hot-melt molding, and includes at least one selected from the group consisting of a phenolic resin, unsaturated polyester resin, diallyl phthalate resin, and polyimide resin.

As the phenolic resin, various resins having a phenol residue as a constituting unit can be used. Examples of the phenolic resin include resins formed by reacting phenols having a phenolic hydroxyl group such as phenol, cresol, xylenol, p-alkylphenol, chlorophenol, bisphenol A, phenol sulfonic acid, resorcinol, and various modified phenols with aldehydes such as formalin and furfural.

The unsaturated polyester resin is formed by reacting an acid component with an alcohol component. Examples of the acid component include unsaturated polybasic acids such as maleic acid, fumaric acid and itaconic acid, or their anhydrides, and aromatic carboxylic acids such as phthalic acid, isophthalic acid and terephthalic acid, or their anhydrides. Examples of the alcohol component include alkylene glycols such as ethylene glycol, diethylene glycol and propylene glycol, and aromatic dials such as bisphenol A and bisphenol A-$C_{2-4}$ alkylene oxide.

Examples of the diallyl phthalate resin include resins obtained from a diallyl phthalate monomer such as diallyl phthalate, diallyl isophthalate, diallyl terephthalate, and diallyl orthophthalate.

The polyimide resin has an imide bond in the main chain of the molecule. The polyimide resin includes at least one selected from the group consisting of a condensation polymer of an aromatic diamine or aromatic diisocyanate and an aromatic tetracarboxylic acid, a bismaleimide resin, which is an addition polymer of an aromatic diamine or aromatic diisocyanate and bismaleimide, a polyammobismaleimide resin, which is an addition polymer of aminobenzoic acid hydrazide and bismaleimide, and a bismaleimide triazine resin composed of a dicyanate compound and a bismaleimide resin.

In the present invention, various conventional additives can be added within the range in which the characteristics of the resin molded article are not impaired. Examples of the additives include a filler agent such as silica and talc; a flame retardant such as antimony oxide, aluminum hydroxide and magnesium hydroxide; a plasticizer such as phthalic acid ester and adipic acid ester; a mold-release agent such as polyethylene wax and silicone oil; and a hydrolysis inhibitor such as carbodiimide. These additives may be used alone or in combination of two or more. The content of the additives is preferably approximately 0.1 parts by mass or more and 50 parts by mass or less in 100 parts by mass of the resin to be injected. It is more preferably 1 part by mass or more and 30 parts by mass or less, still more preferably 5 parts by mass or more and 20 parts by mass or less.

In the present invention, the insert member can be a member that permits formation of a resin molded article by being integrated with the resin injected into the mold. According to the present invention, since the deformation of the insert member during resin molding can be suppressed, it is possible to use an insert member having low pressure resistance. The insert member having low pressure resistance is, for example, an insert member having a hollow portion. As the insert member having a hollow portion, electronic components, tubes, and the like having a hollow portion can be given.

As the electronic components having a hollow portion, a capacitor, a relay, an oscillator, a vibrator, and the like can be mentioned. Resin molding may be performed directly on these electronic components or may be performed after arranging the electronic components on an electronic circuit board.

Under compression load of 100 gf per 1 cm of the length of the tube by a pressure element, the tube preferably has a height in the direction of compression of 7/10 or less of a height in the direction of compression prior to applying compression load. Compression by a pressure element means compression performed by applying surface pressure in the radial direction of the tube. If the height of the tube in the direction of compression under the compression load is 7/10 or less of the height in the direction of compression prior to applying compression load, the flexibility of the tube is improved, and hence the tube can be suitably used for a catheter and the like for which flexibility is required. Therefore, the height of the tube in the direction of compression under the compression load is preferably 7/10 or less, more preferably 6/10 or less, further preferably 5/10 or less, still further preferably 4/10 or less of the height in the direction of compression prior to applying compression load. If the height of the tube in the direction of compression under the compression load is 1/50 or more of the height in the direction of compression prior to applying compression load, it becomes easy to ensure the strength of the tube. Therefore, the height of the tube in the direction of compression under the compression load is preferably 1/50 or more, more preferably 1/40 or more, further preferably 1/30 or more, still more preferably 1/20 or more, still further preferably 1/10 or more of the height in the direction of compression prior to applying compression load.

A raw material of the tube is not particularly limited, but, for example, polyester, polyethylene, vinyl chloride, urethane, silicone rubber, and the like can be used.

Next, an embodiment of a resin molded article obtained by the production method of the present invention will be described with reference to the drawings.

FIGS. 3(a) and 3(b) are plan views of the resin molded article of the invention.

As shown in FIG. 3(a), the resin molded article 5 has tubes 2a and 2b and has a sealed part 6 in which at least part of the tubes 2a and 2b is sealed with resin.

The heights of the tubes 2a and 2b in the direction of compression under compression load of 100 gf per 1 cm of the length of the tube by a pressure element are as described above.

The number of the tubes in the resin molded article 5 is not particularly limited, and only one tube 2c may be included as shown in FIG. 3(b). The resin molded article 5 can include one or more tubes.

Figure 4B:
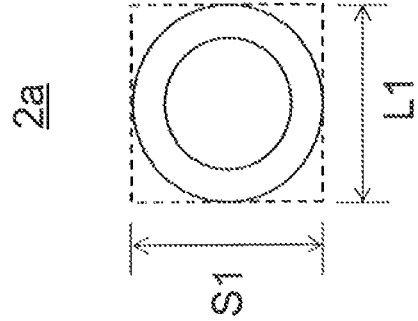
FIG. 4(b) is a cross-sectional view of a tube in the sealed part of FIG. 3(a).
Figure 4A:
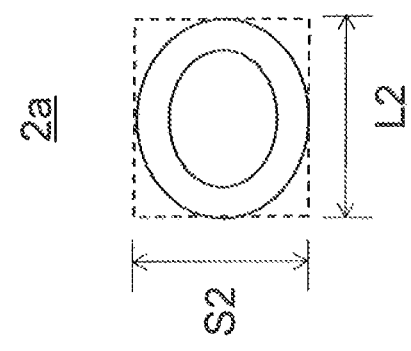
FIG. 4(a) is a cross-sectional view of a tube in the exposed part of FIG. 3(a)

FIG. 4(a) is a cross-sectional view taken along line C-C of the tube 2a in the exposed part of FIG. 3(a). FIG. 4(b) is a cross-sectional view taken along line D-D of the tube 2a in the sealed part of FIG. 3(a). The broken lines in FIGS. 4(a) and 4(b) indicate the circumscribed rectangle of the tube in each cross section.

As shown in FIG. 4(b), the ratio of a minor diameter S2 to a major diameter L2 of the tube 2a in the sealed part 6 is preferably 0.9 or more. By allowing the ratio of the minor diameter S2 to the major diameter L2 to be 0.9 or more, it is possible to improve the liquid sending property and the air feeding property of the tube 2a. Therefore, the ratio of the minor diameter S2 to the major diameter L2 is preferably 0.9 or more, more preferably 0.95 or more, still more preferably 0.98 or more, most preferably 1.0.

The ratio of the minor diameter S2 to the major diameter L2 of the tube 2a (a major and minor diameter ratio in D-D cross section) in the sealed part 6 at a position 1 cm away from one end E of the sealed part 6 in the axial direction of the tube 2a is preferably the same as or smaller than the ratio of a minor diameter S1 to a major diameter L1 of the tube 2a (a major and minor diameter ratio in C-C cross section) in an exposed part 7 that is not sealed with resin at a position 1 cm away from the one end. Specifically, by allowing the major and minor diameter ratio in D-D cross section with respect to the major and minor diameter ratio in C-C cross section to be 0.9 or more, it is possible to reduce a difference in line resistance between the sealing part 6 and the exposed part 7 and to improve the liquid sending property and the air feeding property. The major and minor diameter ratio in D-D cross section with respect to the major diameter to minor diameter ratio in C-C cross section is preferably 0.9 or more, more preferably 0.95 or more, still more preferably 0.98 or more, most preferably 1.0.

The major diameter L1 of the tube 2a in the exposed part 7 is preferably 0.5 mm or more and 10 mm or less. By setting the major diameter L1 to be 0.5 mm or more, the liquid sending property and the air feeding property can be easily improved. The major diameter L1 is more preferably 1 mm or more, further preferably 2 mm or more. By setting the major diameter L1 to be 10 mm or less, insertion into the body or the like is easily performed. The major diameter L1 is more preferably 7 mm or less, further preferably 5 mm or less.

The preferred ratio of the major diameter and the minor diameter of the tube 2b and the preferred length of the major diameter are the same as those of the tube 2a.

The minimum thickness of the tubes 2a and 2b in the sealed part 6 is preferably 0.05 mm or more and 0.5 mm or less. By setting the minimum thickness to be 0.05 mm or more, the strength of the tubes 2a and 2b can be improved. The minimum thickness is more preferably 0.07 mm or more, further preferably 0.15 mm or more. By setting the minimum thickness of the tubes 2a and 2b in the sealed part 6 to be 0.5 mm or less, the liquid sending property and the air feeding property can be easily improved. The minimum thickness is preferably 0.5 mm or less, more preferably 0.4 mm or less, further preferably 0.3 mm or less.

The thickness of the resin of the sealed part 6 is preferably 0.5 mm or more and 20 mm or less. By setting the thickness of the resin of the sealed part 6 to be 0.5 mm or more, the strength of the sealed part 6 can be improved, and leaks of liquid or gas can be suppressed. The thickness of the resin of the sealed part 6 is preferably 0.5 mm or more, more preferably 1 mm or more, further preferably 2 mm or more. By setting the thickness of the resin of the sealed part 6 to be 20 mm or less, the weight of the resin molded article 5 can be reduced. The thickness of the resin of the sealed part 6 is preferably 20 mm or less, more preferably 10 mm or less, further preferably 5 mm or less.

The number of bores in each of the tubes 2a and 2b is not limited to one, and may be two or more.

Preferably, the tubes 2a and 2b have a branched part, and the branched part is sealed with resin. By being provided with the branched part, the resin molded article 5 has an increased number of applications, and by sealing the branched part with resin, leaks of liquid or gas from the branched part can be suppressed.

The shape of the sealed part 6 is not particularly limited, and examples thereof include a polygonal pillar shape, a cylindrical shape, and a shape provided with a convex portion and a concave portion on these shapes. One or more convex portions or concave portions may be provided. In addition, a through hole may be provided in the convex portion of the sealed part 6 in order to facilitate attachment of the resin molded article 5 to a device and clothes or the like of a patient.

The resin molded article 5 can be used, for example, as a catheter. Examples of the catheter include a central venous catheter, angiographic catheter, balloon catheter, cardiac catheter, angiographic catheter, and the like.

The resin molded article 5 is preferably an injection molded article obtained by injection molding. The use of injection molding allows mass production, whereby the resin molded article 5 can be provided at low prices.

This application claims the benefit of priority to Japanese Patent Application No. 2016-256476, filed on Dec. 28, 2016. The entire contents of the specifications of Japanese Patent Application No. 2016-256476, filed on Dec. 28, 2016 are incorporated herein by reference.

EXPLANATION OF REFERENCES NUMERALS

1 Insert member
2a to 2c Tube
5 Resin molded article
6 Sealed part
7 Exposed part
10 Mold
10a Lower mold
10b Upper mold
11 Sprue
12 Runner
13 Gate
14 Cavity
15a, 15b Overflow portion
16a, 16b Recess

The invention claimed is:

1. A method for producing a resin molded article, the method comprising the steps of:
disposing an insert member in a cavity of a mold;
performing injection of molten resin into the cavity;
terminating the injection on and after the molten resin reaches an overflow portion in the cavity and before the molten resin fills the overflow portion; and
separating resin in the overflow portion,
wherein:
the insert member is one or more tubes,
no core bar is inserted into the one or more tubes, and
under compression load of 100 gf per 1 cm of a length of the one or more tubes by a pressure element, the one or more tubes have a height in a direction of compression of 7/10 or less of a height in the direction of compression prior to applying the compression load.

2. The method for producing a resin molded article according to claim 1, wherein a molding temperature is 100° C. or higher and 250° C. or lower.

3. The method for producing a resin molded article according to claim 1, wherein a pressure of the injection is 0.1 MPa or more and 50 MPa or less.

4. The method for producing a resin molded article according to claim 1, wherein a pressure applied onto the insert member after the injection is 5 MPa or less.

5. The method for producing a resin molded article according to claim 1, wherein a melt viscosity at 200° C. of the resin is 5 dPa·s or more and 5000 dPa·s or less.

6. The method for producing a resin molded article according to claim 1, wherein the resin is at least one hot-melt resin selected from a group consisting of a polyester-based hot-melt resin, polystyrene-based hot-melt resin, polyolefin-based hot-melt resin, polyurethane-based hot-melt resin, polyamide-based hot-melt resin, and reactive hot-melt resin.

7. The method for producing a resin molded article according to claim 1, wherein the resin is at least one thermosetting resin selected from a group consisting of a phenolic resin, unsaturated polyester resin, diallyl phthalate resin, and polyimide resin.

8. A resin molded article comprising one or more tubes and a sealed part in which at least part of the one or more tubes is sealed in resin,
wherein, under compression load of 100 gf per 1 cm of a length of the one or more tubes by a pressure element, the one or more tubes have a height in a direction of compression of 7/10 or less of a height in the direction of compression prior to applying the compression load, and
a ratio of a minor diameter to a major diameter of the one or more tubes in the sealed part at a position 1 cm away from one end of the sealed part in an axial direction of the one or more tubes is smaller than a ratio of a minor diameter to a major diameter of the one or more tubes in an exposed part that is not sealed in the resin at a position 1 cm away from the one end.

9. The resin molded article according to claim 8, wherein a ratio of the minor diameter to the major diameter of the one or more tubes in the sealed part is 0.9 or more.

10. The resin molded article according to claim 8, wherein the one or more tubes in the sealed part have a minimum thickness of 0.05 mm or more and 0.5 mm or less.

11. The resin molded article according to claim 8, wherein the one or more tubes have a branched part, and the branched part is sealed in the resin.

12. The resin molded article according to claim 8, wherein the resin molded article is an injection molded article.

* * * * *